United States Patent [19]
Straits et al.

[11] Patent Number: 5,554,132
[45] Date of Patent: Sep. 10, 1996

[54] HAND GRIP FOR USE WITH SYRINGE

[75] Inventors: Thomas D. Straits, Grayslake; Andrew D. Obecny, Antioch; Kenneth R. Greene, Vernon Hills, all of Ill.

[73] Assignee: Abbott Laboratories, Abbott Park, Ill.

[21] Appl. No.: 413,562

[22] Filed: Mar. 30, 1995

[51] Int. Cl.⁶ .................................................. A61M 5/00
[52] U.S. Cl. ............................................. 604/227; 604/187
[58] Field of Search ................................... 604/227, 228, 604/187, 218, 233, 223

[56]      References Cited

U.S. PATENT DOCUMENTS

| | | | |
|---|---|---|---|
| 4,687,472 | 8/1987 | Gross | 604/223 |
| 4,925,449 | 5/1990 | Saez et al. | 604/218 X |
| 5,241,969 | 9/1993 | Carson et al. | 604/227 X |

FOREIGN PATENT DOCUMENTS 614495   2/1961   Canada ................................ 604/227

*Primary Examiner*—John D. Yasko
*Attorney, Agent, or Firm*—Brian R. Woodworth

[57]              ABSTRACT

The hand grip device of the present invention is designed for use with an associated syringe having a plunger stem with a push and pull flange at a terminal end of the plunger stem. The hand grip device includes a grip portion extending generally the width of a hand and having opposite ends. A C-shaped bracket portion includes two arms and a push bar. Each arm is connected to the opposite ends of the grip portion and the push bar connects the two arms so as to be generally parallel to the grip portion. A pull bar is spaced from and parallel to the push bar. The pull bar is cantilevered from conveniently the lower bracket arm and has a V-shaped slot extending away from the cantilevered arm for slidably engaging the push-pull flange of the associated syringe.

8 Claims, 3 Drawing Sheets

HAND GRIP FOR USE WITH SYRINGE

TECHNICAL FIELD

The present invention relates generally to a hand grip device for use with a syringe, and more particularly, to a ergonomically designed hand grip device which reduces the repetitive motion injury to a user caused by repeated aspiration and/or administration using a syringe.

BACKGROUND OF THE INVENTION

Pharmacies, hospitals, medical clinics, veterinarians, and many industrial or manufacturing operations utilize standard plastic syringes in their operations. These empty syringes can be used for both aspiration (i.e., filling the syringe) and administration (i.e., expelling the contents of the syringe). To aspirate with a syringe, a portion of the plunger stem is grasped between the thumb and the index finger with a pinch grip and the stem and plunger are pulled to the rear. To inject the contents of the syringe, typically the user grasps the syringe barrel between the index finger and the middle finger and pushes on the stem with his thumb. Often these operations are repeated numerous times, as for example during filling or reconstitution of drugs in hundreds of syringes or IV containers in a hospital pharmacy. As another example, syringes may be used to evacuate the lungs of hundreds of test animals in a research laboratory.

Thus, repetitive operations of this nature are common in the medical field such as pharmacies that dispense intravenous drug products, in laboratories that conduct research tests, as well as other diverse industrial and manufacturing operations. The repetitive motion in these operations often leads to repetitive motion injuries such as strained thumbs or carpal tunnel syndrome.

The most accepted alternative to manual manipulation of syringes has been electromechanical pumps. However, in the medical field the pump sets require frequent and expensive set changes. Pumps and pump sets are rarely justified except in high volume, repetitive pharmacy operations.

The present hand grip for use with a syringe has been particularly configured to facilitate efficient and convenient preparation and administration of solutions and samples while minimizing the user's susceptibility to repetitive motion injuries.

SUMMARY OF THE INVENTION

The hand grip device of the present invention is designed for use with an associated syringe having a plunger stem with a push and pull flange at a terminal end of the plunger stem. The hand grip device includes a grip portion extending generally the width of a hand and having opposite ends. A C-shaped bracket portion includes two arms and a push bar. Each arm is connected to the opposite ends of the grip portion and the push bar connects the two arms so as to be generally parallel to the grip portion. A pull bar is spaced from and parallel to the push bar. The pull bar is cantilevered from the lower bracket arm and has a V-shaped slot extending away from the cantilevered arm for slidably engaging the push-pull flange of the associated syringe.

Preferably, the grip portion of the hand grip device is ergonomically angled approximately 12° from the perpendicular to the axial motion line of the syringe plunger and hand grip device. The entire hand grip system is preferably integrally molded of a suitable, medical grade thermoplastic for use in a clean room environment.

Other features and advantages of the present hand grip system will become readily apparent from the following detailed description, the accompanying drawings, and the appended claims.

DETAILED DESCRIPTION

Figure 1:
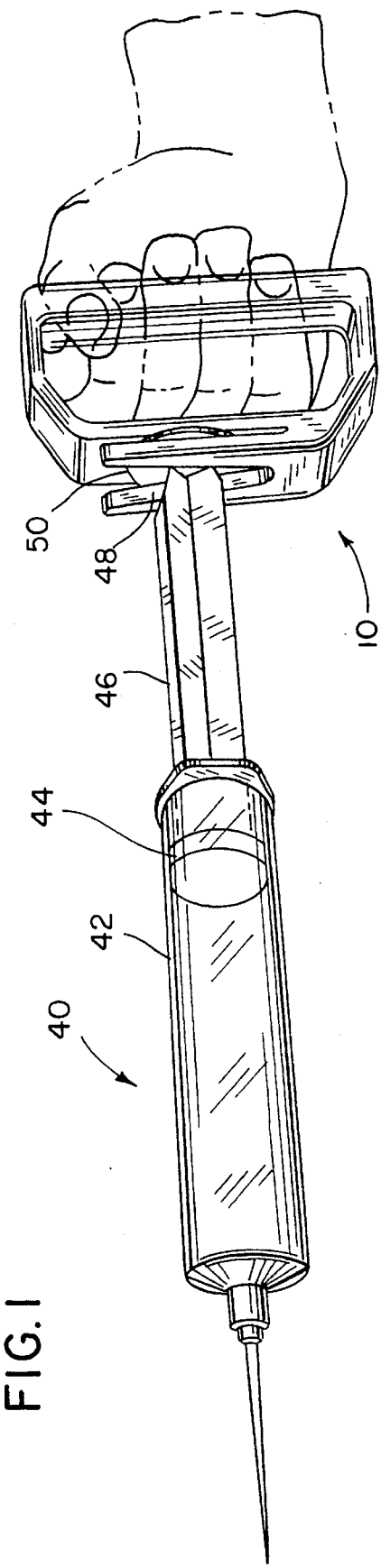
FIG. 1 is perspective view of the hand grip device as used with an associated syringe.
Figure 3:
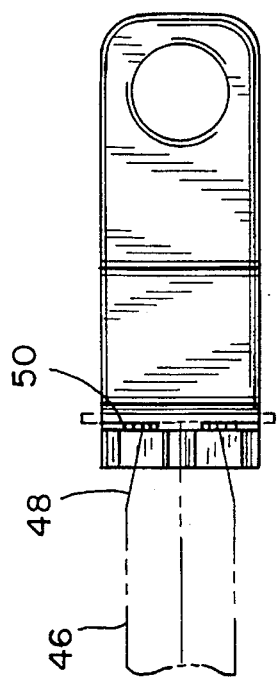
FIG. 3 is a top view of the hand grip device.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiments illustrated.

With reference first to FIG. 1, therein is illustrated a hand grip device 10 embodying the principals of the present invention. As will be further described, the present hand grip releasably secures a typical syringe plunger stem so that the user can fill and expel solution from the syringe with a closed fist power grip rather than thumb and index finger pinch grip.

Figure 2:
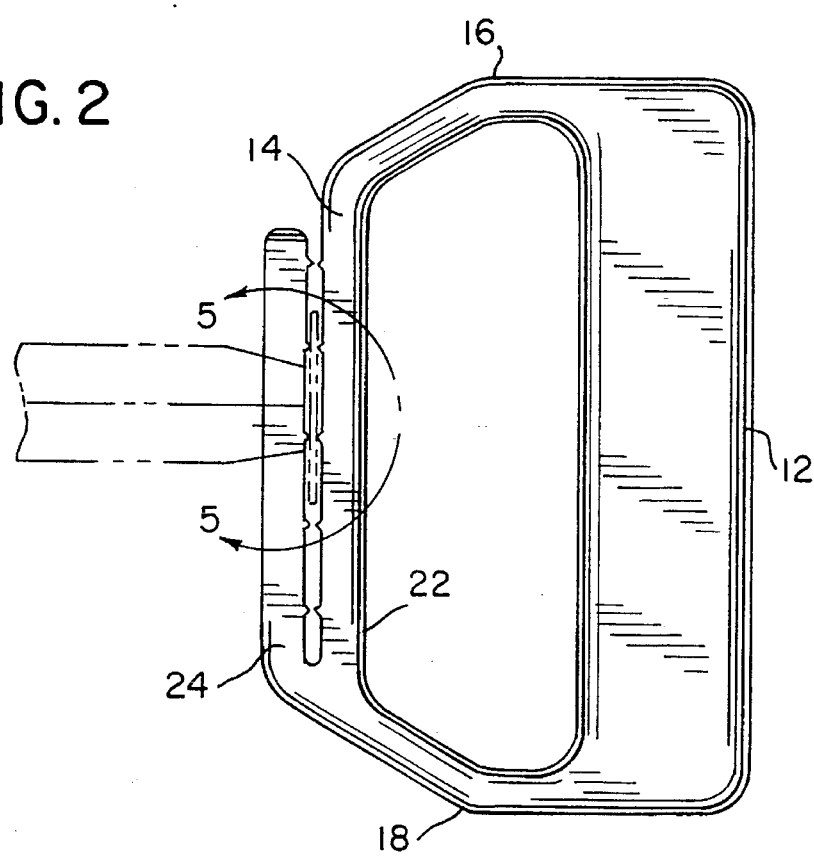
FIG. 2 is a side view of the hand grip device.

With particular reference to FIG. 2, the hand grip device includes a grip portion 12 extending generally the width of an adult hand as for example shown in FIG. 1. The two opposite ends of the grip portion are connected by a C-shaped bracket portion 14. The bracket includes two arms 16 and 18 and a push bar 22. The upper and lower arms are connected to opposite ends of the hand grip portion and the push bar is connected between the two arms so as to be generally parallel to the grip portion. A pull bar 24 is spaced from and parallel to the push bar. The pull bar is cantilevered from one of the bracket arms, preferably, the lower bracket arm 18.

Figure 4:
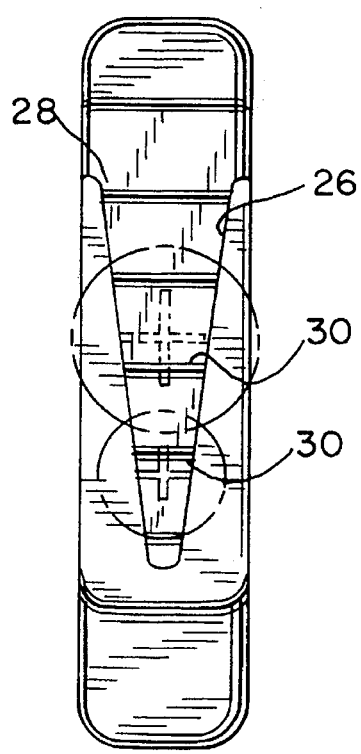
FIG. 4 is a front view showing in phantom two different sizes of releasably secured syringe plunger stems.
Figure 5:
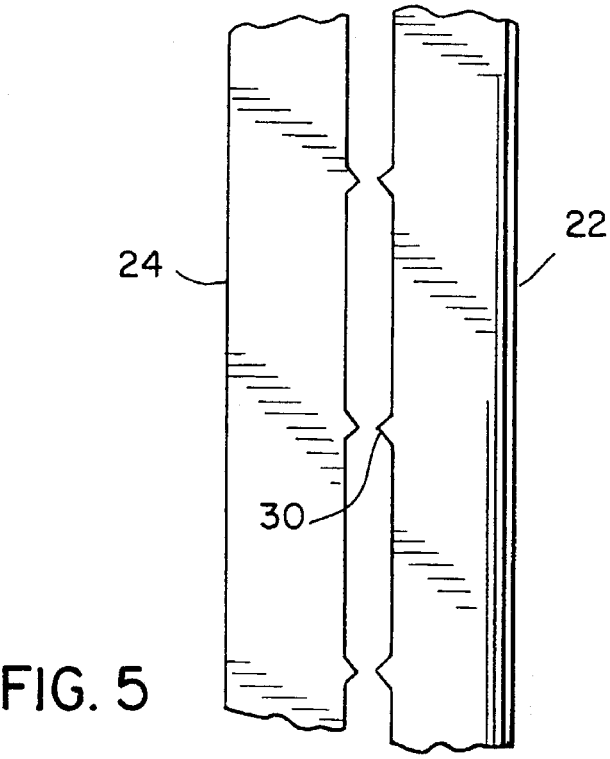
FIG. 5 is an enlarged view of a portion of FIG. 2.

As best seen with reference to FIG. 4, the pull bar has a V-shaped slot 26 extending away from the cantilevered and to an open end 28 for slidably engaging the push and pull flange of an associated syringe. The push bar further includes a plurality of raised ribs 30 on the push bar. The ribs are parallely spaced and are intended to releasably secure the push pull flange of the associated syringe as will be presently explained.

The typical syringe 40 as shown in FIG. 1, includes a cylindrical barrel 42 having a delivery end and an open end. The open end is sealed by a slidable plunger piston 44. A plunger stem 46 extends from the piston and has a length at least the length of the syringe barrel. Typically, the stem tapers inward 48 at the distal end portion of the stem to a perpendicular flange 150 that can be used to push or pull the plunger stem as required. The flange 150 is typically the same diameter as the diameter of the syringe barrel.

In operation, the V-shaped slot 26 easily engages the push and pull flange 150 of the syringe. The syringe user may then grip the device with a closed fist hand grip as shown in FIG.

I and efficiently and safely pull and push the syringe plunger as required by the procedure.

As shown in FIG. 4, the V-shaped slot allows syringes of different volumes having different sized push and pull flanges to be secured within the push and pull bars. For example, the two illustrated flanges are from 10cc and 20cc syringes. A further feature of the present hand grip are the holding ribs 30 on the push bar 22 of the hand grip. These holding ribs are spaced parallel to each other so that at least one rib is frictionally engaged by the push and pull flange of an associated syringe when the flange is slid into engagement between the push bar and the pull bar. The holding ribs prevent the syringe push and pull flange from accidentally slipping out of the hand grip, but does allow the push and pull flange to be readily disengaged when desired.

The hand grip device of the present invention is preferably integrally molded of a medical grade thermoplastic such as an acetal plastic. For example, Delrin® made by DuPont, is easily cleaned and tolerant of medical cleaning agents. Thus, a device so constructed is suitable for use in a clean room environment or in a pharmacy luminar flow hood.

Figure 6:
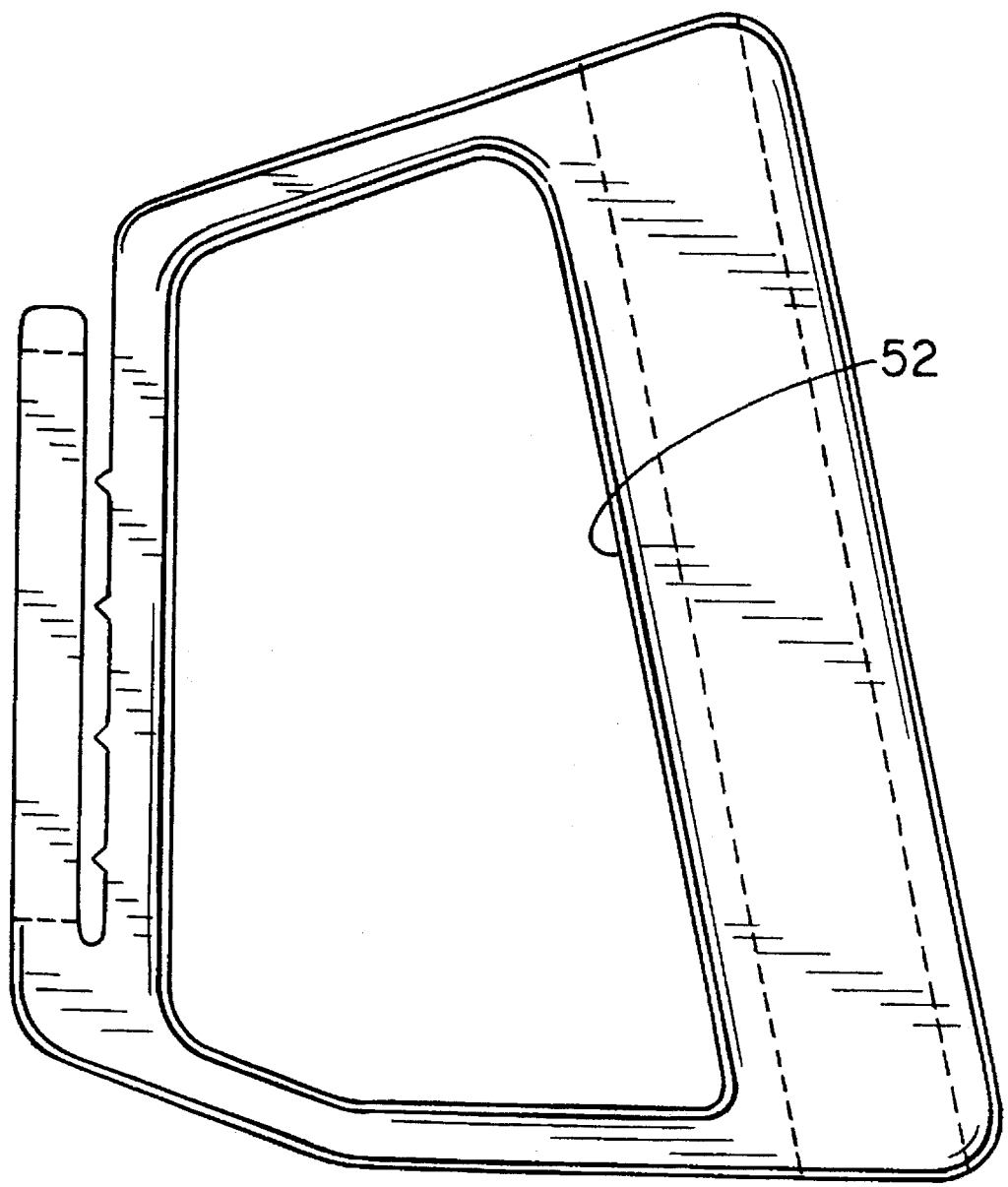
FIG. 6 is a side view a preferred embodiment of the hand grip device.

In a preferred embodiment shown in FIG. 6, the hand grip device includes a grip portion 52 that is ergonomically angled from the perpendicular to accommodate the hand grip centerline of the motion axis of the plunger stem. Preferably, the grip portion is angled 12° from the perpendicular.

The use of the hand grip of the present invention for preparation and administration by syringe is believed to reduce the traditional repetitive motion injury to a syringe user caused by the repeated aspiration and administration of a syringe when using a pinch grip.

From the foregoing, it will be observed that numerous modification and variations can be effected without departing the true spirit and scope of the novel concept of the present invention. The present disclosure is to be understood that no limitations with respect to the specific embodiments herein is intended or should be inferred. The disclosure is intended to cover, by appended claims, all such modifications as fall within the scope of the claims.

What is claimed is:

1. A hand grip device for use with an associated syringe having a plunger stem with a push and pull flange at a terminal end of the plunger stem, comprising:

a grip portion having opposite ends and extending generally the width of a hand;

a bracket portion including two arms and a push bar, each arm connected to opposite ends of the grip portion and the push bar connecting the two arms so as to be generally parallel to the grip portion; and a pull bar spaced from and parallel to the push bar and cantilevered from one of the bracket arms, the pull bar having a V-shaped slot extending away from the cantilevered end to an open end for slidably engaging the push and pull flange of the associated syringe.

2. The hand grip of claim 1 further including means on the push bar for releasably securing the push and pull flange of the associated syringe between the push bar and the pull bar.

3. The hand grip device of claim 2 wherein the securing means includes a plurality of raised ribs on the push bar parallely spaced so that at least one rib is frictionally engaged by the push and pull flange of the associated syringe when the flange is slid into engagement between the push bar and the pull bar.

4. The hand grip device of claim 3 wherein the hand grip device is integrally molded of a thermoplastic.

5. The hand grip device of claim 4 wherein the thermoplastic is a medical grade plastic such as Delrin® plastic.

6. The hand grip device of claim 1 wherein the grip portion is ergonomically angled from the perpendicular to the motion axis of the plunger stem of the associated syringe.

7. The hand grip device of claim 6 wherein the grip portion is angled 12° from the perpendicular to the plunger stem of the associated syringe.

8. The hand grip device of claim 1 wherein the grip portion reduces the repetitive motion injury to a syringe user caused by repeated aspiration and administration of a syringe.

* * * * *